United States Patent

Meyer

(10) Patent No.: US 8,961,175 B2
(45) Date of Patent: Feb. 24, 2015

(54) DENTAL VACUUM

(75) Inventor: Robert A. Meyer, Spearfish, SD (US)

(73) Assignee: Foxhammer Inc., Spearfish, SD (US)

(*) Notice: Subject to any disclaimer, the term of this patent is extended or adjusted under 35 U.S.C. 154(b) by 49 days.

(21) Appl. No.: 13/470,791

(22) Filed: May 14, 2012

(65) Prior Publication Data

US 2012/0288821 A1    Nov. 15, 2012

Related U.S. Application Data

(60) Provisional application No. 61/485,182, filed on May 12, 2011.

(51) Int. Cl.
A61C 17/12    (2006.01)
A61C 19/00    (2006.01)

(52) U.S. Cl.
CPC ..................... *A61C 19/007* (2013.01)
USPC .......................................................... 433/92

(58) Field of Classification Search
USPC .............. 433/91–97, 216; 210/138, 143, 188, 210/259, 295, 311, 314, 335; 96/134, 156, 96/189, 190, 219, 421; 55/315, 318, 319, 55/350.1, 385.1, 385.2, 482, 485, 466, 55/421, 302, 324, 356; 15/314
See application file for complete search history.

(56) References Cited

U.S. PATENT DOCUMENTS

| | | | |
|---|---|---|---|
| 2,784,717 A * | 3/1957 | Thompson | 604/245 |
| 3,012,323 A * | 12/1961 | Thompson | 433/92 |
| 3,735,491 A * | 5/1973 | Pabalan, Jr. | 433/93 |
| 4,385,891 A * | 5/1983 | Ligotti | 433/92 |
| 4,963,094 A | 10/1990 | Meyer | |
| 5,017,135 A | 5/1991 | Meyer | |
| 5,282,744 A | 2/1994 | Meyer | |
| 5,311,640 A | 5/1994 | Holland | |
| 5,407,565 A * | 4/1995 | Austin et al. | 210/188 |
| 5,779,472 A | 7/1998 | Meyer | |
| 5,885,076 A * | 3/1999 | Ralls et al. | 433/92 |
| 5,908,297 A | 6/1999 | Fill et al. | |
| 5,967,780 A | 10/1999 | Morrissey | |
| 6,203,590 B1 * | 3/2001 | Byrd et al. | 55/319 |
| 6,409,803 B1 | 6/2002 | Tremel et al. | |
| 6,464,499 B1 * | 10/2002 | Lu | 433/92 |
| 6,638,066 B2 | 10/2003 | Hubner et al. | |
| 6,790,038 B2 | 9/2004 | Hubner et al. | |
| 6,925,886 B2 | 8/2005 | Meyer | |
| 7,076,398 B2 | 7/2006 | Meyer et al. | |
| 7,156,896 B2 | 1/2007 | Schenk et al. | |
| 7,306,460 B2 | 12/2007 | Hubner et al. | |
| 2005/0020966 A1 * | 1/2005 | Soring et al. | 604/22 |
| 2007/0163964 A1 * | 7/2007 | Williamson et al. | 210/736 |

* cited by examiner

*Primary Examiner* — Cris L Rodriguez
*Assistant Examiner* — Justin O'Donnell
(74) *Attorney, Agent, or Firm* — Nixon & Vanderhye P.C.

(57) ABSTRACT

An in-treatment room dental vacuum system includes a vacuum producer and an operator tool including an evacuator tip. A separator is coupled with the vacuum producer and is disposed between the vacuum producer and the operator tool. A hose assembly connects the operator tool and the separator. In use, the separator receives material from the operator tool via the hose assembly and separates the material into wet phase material and dry phase material.

17 Claims, 2 Drawing Sheets

DENTAL VACUUM

CROSS-REFERENCES TO RELATED APPLICATIONS

This application claims the benefit of U.S. Provisional Patent Application Ser. No. 61/485,182, filed May 12, 2011, the entire content of which is herein incorporated by reference.

STATEMENT REGARDING FEDERALLY SPONSORED RESEARCH OR DEVELOPMENT (Not Applicable)

BACKGROUND OF THE INVENTION

The invention relates to a dental vacuum system and, more particularly, to an in-treatment room dental vacuum system that provides for efficient operation with low power requirements, low maintenance and easily manageable, safe discharge.

Many dental procedures require removing unwanted materials from the operating field. Removal actions are needed to improve visibility and to protect the patient from aspirating or swallowing dental materials or biological residue. Dental vacuum systems were created to meet this need.

Initially the "dental vacuum system" consisted of a simple aspirating bulb. Later, water venturi systems were used. By the mid-1900s, electrically powered, devices similar to vacuum cleaners began to appear in many U.S. dental treatment rooms. These devices were noisy, produced poor flow and were subject to short service lives.

Central dental vacuum systems, in which vacuum source equipment is located outside of the treatment room, became common starting in the early 1960s. In central dental vacuum systems, the equipment is out-of-sight, sometimes out of hearing range, and often out-of-mind.

Water ring pumps became the favored vacuum producing technology for smaller systems as they produced strong vacuum, were compact and relatively inexpensive to purchase. However, as water quality and availability, as well as increasing water and sewer costs began to complicate the ownership of water ring pumps, water-free systems gained in popularity. In the 1990s, the RAMVAC Dental Vacuum System successfully challenged existing concepts of dental vacuum system costs, durability and performance and soon sold more dollars worth of water-free dental vacuum systems in the U.S. than all other water-free systems combined.

Dental vacuum systems are associated with two categories of well documented safety concerns. The first category involves the environmental impact of system discharges known to contain significant amounts of mercury. The second category involves the safety of dental treatment room personnel exposed to fugitive aerosols and gases produced during dental procedures. These fugitive materials could be, but are often not, captured by the dental vacuum system.

In addition to safety concerns associated with dental vacuum in general, there are numerous and serious, generally unrealized drawbacks to central systems.

BRIEF SUMMARY OF THE INVENTION

The system according to embodiments of the invention involves a return to placing the entire system in the treatment room. Recent technology advances now allow for smaller, quieter, more durable vacuum producers that can avoid the limitations of original treatment room located systems.

The system achieves major advances in dental vacuum by reducing overall cost of ownership, improving safety, simplifying system sizing and eliminating costly vacuum piping. However, it must overcome some mundane challenges in order to immediately become an attractive alternative to existing central system: it should be small enough, quiet enough and its price point should be reasonable. The system components should be selected and/or developed to insure the system meets these challenges.

In an exemplary embodiment, an in-treatment room dental vacuum system includes a vacuum producer and an operator tool including an evacuator tip. A separator is coupled with the vacuum producer and is disposed between the vacuum producer and the operator tool. A hose assembly connects the operator tool and the separator. In use, the separator receives material from the operator tool via the hose assembly and separates the material into wet phase material and dry phase material.

The vacuum producer may be a fan/motor unit and may be a 0.5 hp or smaller motor, where the operator tool, hose assembly and separator comprise head loss components that effect a target performance value of at least 20 SCFM at the evacuator tip.

The separator may include an inlet receiving a flow of the material from the operator tool via the hose assembly; a wet phase filter assembly that receives liquids and heavy solids from the flow, the wet phase filter assembly including a wet filter cartridge; and a dry phase filter assembly that receives gases, aerosols and light solids from the flow, the dry phase filter assembly including a dry filter cartridge. In this context, the wet phase filter assembly may include a strainer, a coarse filter disposed downstream of the strainer, and a fine filter disposed downstream of the coarse filter. The coarse filter and the fine filter may be housed in the wet filter cartridge. The wet filter cartridge may be removable from the wet phase filter assembly. The wet phase filter assembly may include a first conduit that extends from a liquid buffer space downstream of the strainer to a bottom of the coarse filter. In this context, the wet phase filter assembly may additionally include a second conduit that extends from a coarse filter output space to a bottom of the fine filter. The dry phase filter assembly includes a plurality of filters arranged in series. The filters may be a dust filter, a HEPA filter, and an activated carbon filter. The plurality of filters may be housed in the dry filter cartridge. In this context, the dry filter cartridge may be removable from the dry phase filter assembly.

The system may additionally include a controller cooperable with the vacuum producer and the separator, and structure that communicates with the controller for determining that the wet filter cartridge and the dry filter cartridge require replacement. The determining structure may include a timer that measures a use time and signals that cartridge replacement is needed after a predetermined use time has elapsed. The determining structure may include a differential pressure sensor disposed across an inlet and an exhaust of the dry phase filter assembly.

The hose assembly may include multiple diameters with an operator hose having a first diameter coupled with the operator tool and a connection hose having another diameter larger than the first diameter coupled with the operator hose. Preferably, the first diameter is about ⅝", and the other diameter is about 1".

In another exemplary embodiment, an in-treatment room dental vacuum system includes a motor having an hp value less than 0.5, where the motor serves as a vacuum producer;

a separator coupled with the motor; and an operator tool coupled with the separator via a hose assembly. The operator tool includes an evacuator tip. The operator tool and the hose assembly are constructed to effect a head loss component such that the motor produces a vacuum with a target performance value of at least 20 SCFM at the evacuator tip. The separator receives material from the operator tool via the hose assembly, separates the material into wet phase material and dry phase material, separately filters the wet phase material and the dry phase material, discharges filtered wet phase material to a drain, and exhausts filtered dry phase material into the treatment room. The hose assembly may include an operator hose having a first diameter coupled with the operator tool and a connection hose having a second diameter larger than the first diameter coupled with the operator hose.

In yet another exemplary embodiment, a method of removing and processing material from a dental field includes the steps of generating a vacuum pressure on an evacuator tip of an operator tool; removing the material from the dental field with the evacuator tip; guiding the material via a hose assembly to a separator; separating the material with the separator into wet phase material and dry phase material; filtering the wet phase material using a wet phase filter assembly; filtering the dry phase material using a dry phase filter assembly; discharging the filtered wet phase material to a drain; and exhausting the filtered dry phase material into the treatment room.

BRIEF DESCRIPTION OF THE DRAWINGS

These and other aspects and advantages will be described in detail with reference to the accompanying drawings, in which.

DETAILED DESCRIPTION OF THE INVENTION

Unlike the prior central dental vacuum systems, the system of the preferred embodiments is a self-contained system that is constructed for in-treatment room use. A dental practice would thus use the dental system of the described embodiments in each treatment room of its facility.

Figure 1:
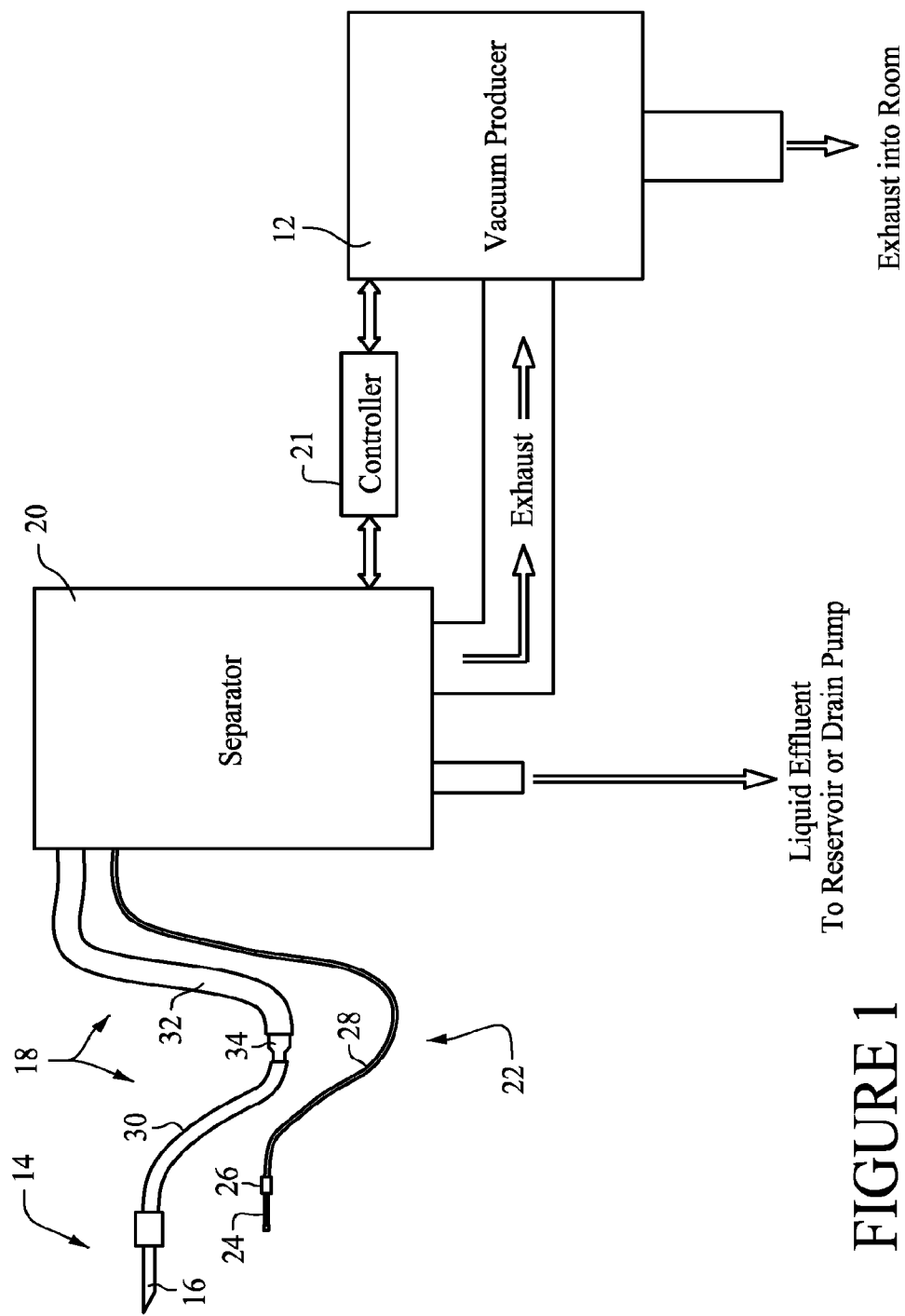
FIG. 1 is a schematic diagram of the in-treatment room dental vacuum system of the described embodiments.

FIG. 1 is a schematic diagram of the dental vacuum system. A vacuum producer 12 generates a negative pressure (vacuum pressure) through the system. An operator tool 14 includes an evacuator tip (HVE tip) 16, and a hose assembly 18 connects the operator tool 14 to a separator 20. The separator 20 receives material from the operator tool 14 via the hose assembly 18 and separates the material into wet phase material and dry phase material. A controller 21 is cooperable with the vacuum producer 12 and the separator 20 to control operation of the system components. The system also includes a saliva ejector assembly 22 including a saliva ejector tip 24, a saliva ejector holder 26 and a saliva ejector hose 28. The saliva ejector assembly is a low flow (typically less than ⅕ the HVE flow) dental vacuum tool not intended to evacuate gases but rather intended to evacuate liquids and relatively small particulates from the operating field.

As the vacuum producer 12, it is preferable to utilize a fan/motor unit. There is currently a wide selection of well-developed fan/motor units available. In general, fans cost less than water ring and other positive displacement pumps. Fans produce high flow rates at relatively low vacuum strength, thus should be used in conjunction with low head loss components in order to achieve target performance values. In this context, a preferred construction of the fan/motor unit for the vacuum producer 12 is a 0.5 HP motor. It has been discovered that the operator tool 14, the hose assembly 18, and the separator 20 can be constructed to define a head loss component that effects a target performance value of at least 20 SCFM at the evacuator tip 16. The reduced horsepower of the vacuum producer 12 results in reduced power requirements. Other features that serve to reduce power requirements include the ability of the controller 21 to turn the vacuum producer 12 on only when vacuum is needed, the elimination of head loss in a fixed piping system, and the elimination of a need to supply vacuum to multiple simultaneous operators. The power requirements can be reduced as much as 75% as compared with existing systems. The target performance value of at least 20 SCFM amounts to an increase of nearly 300% over existing systems, which typically run continuously in order to produce 5-7 SCFM at the evacuator tip. Additionally, conventional systems use fan/motor units with considerably higher horsepower.

Design objectives for the fan/motor unit are provided in Table 1.

| Monitoring Functions | |
| --- | --- |
| Power | AC power available |
| HVE mode | Fan motor on, running in HVE Mode (full output) |
| SE mode | Fan motor on, running in SE Mode (reduced output) |
| Motor off | Fan motor off |
| Alarm | Moisture in normally dry location |
| Dry Filter | Status: ok, nearing capacity (plan to replace), replacement needed |
| Wet Filter | Status: ok, nearing capacity (plan to replace), replacement needed |
| Manual | Fan motor switch on manually |
| Hours | Run time hour meter |
| Control Functions | |
| Auto On/Off | Fan-motor controlled by switches in HVE and saliva ejector holders |
| Manual On/Off | Fan-motor controlled by switches on HVE and saliva ejector tip hose to tip adapters, overrides Auto "off", turns on motor and "manual" mode indicator |
| Moisture switch | Activated by moisture present in normally dry location, shuts off motor, turns on "alarm" indicator |
| Wet Filter switch | Activated by amount of material accumulated in wet filter, turns on "Wet Filter" status indicator, turns off motor when replacement is needed |
| Dry Filter switch | Activated by amount of material accumulated in dry filter, turns on "Dry Filter" status indicator, turns off motor when replacement is needed |

The controller or control system 21 provides digital switching and monitoring of the vacuum producer 12 and monitoring of other components in the separator 20. Design objectives for the controller 21 are provided in Table 2.

| | |
|---|---|
| Flow Performance | Min 20 SCFM @ 4 in Hg (54.4 in H$_2$O) |
| Type of material handled | moist air |
| Drive | Preferable direct drive, rapid start |
| | Preferable low voltage (12 or 24) motor desired, 115 vac/200 vac, 50/60 Hz ok |
| Physical Size | Approx 64 cu in (fan/motor assembly) |
| Noise | Less than 50 dBA (measured immediately outside enclosure) |
| Operating temperature | Standard: 104° F. to 32° F. (40° C. to 0° F.) |
| | Optional: 140° F. to 32° F. (60° C. to 0° F.) |
| Efficiency | Standard or better |
| Service Life | Greater than 1,000 hrs |
| Duty cycle | Capable of 100% |
| | Normally 25% |
| Speed | Inverter or discrete "idle/saliva ejector" and HVE mode |

The HVE tip 16 of the operator tool 14 is preferably removable and either sterilizable or disposable. The tip 16 is the inlet to the vacuum system and contacts the patient. As noted, the vacuum producer 12 meets the target performance value of at least 20 SCFM at the evacuator tip 16. The evacuator tip thus serves to remove material from a dental field in a patient's mouth. HVE tips exist in many sizes and shapes and are sold by many vendors. Details of the HVE tip 16 will thus not be further described. In order to better control head loss and, more importantly, to mitigate possible unwanted noise associated with the increased flow rates of the present system, it is desirable to use a highly engineered HVE tip as an integral part of the system.

The hose assembly 18 transports material entering the vacuum system to the separator 20. The inside diameter, length and cross-section of the hose assembly and its connector to fixed piping are typically major sources of dental vacuum system head loss. Hoses with inside diameters that are too small and lengths needlessly long significantly increase losses. However, to increase hose diameters risks an increase in weight and unwieldy loss of flexibility, thus increasing operator fatigue and frustration.

The hose assembly 18 in the present system includes multiple hoses of different inside diameters to reduce losses while maintaining flexibility. The hose assembly 18 includes an operator hose 30 having a first diameter coupled with the operator tool 14. A connection hose 32 has a second diameter larger than the first diameter and is coupled with the operator hose 30 via a hose adapter 34. In an exemplary construction, the first diameter is about ⅝", and the second diameter is about 1". The smaller diameter operator hose 30 closer to the evacuator tip 16 serves to reduce the weight of the hose and improve flexibility. The connection hose 32, farther away from the tip, is typically not lifted or moved by operator activity and thus can be a larger diameter to decrease head loss. The connector/adapter 34 is preferably a low head loss connector.

It has been discovered that increases in hose diameter result in an exponential decrease in head loss (i.e., to the order of a 5$^{th}$ power). Conventional HVE hoses have an inside diameter of about ½". With the increase to ⅝", for example, for the operator hose 30, the head loss can be substantially reduced. Head losses are further reduced with the still larger diameter connection hose 32.

Figure 2:
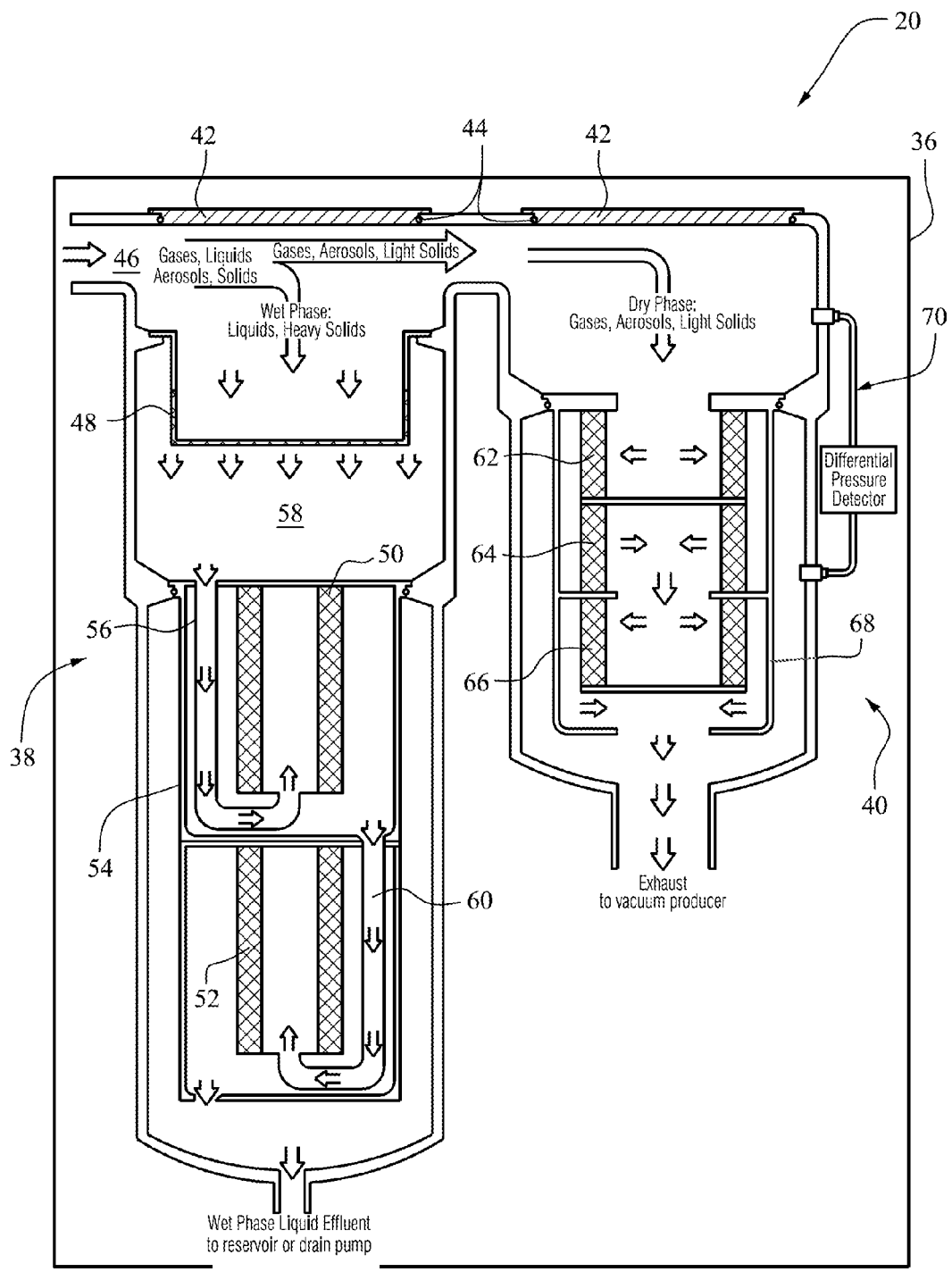
FIG. 2 is a schematic diagram of the separator.

With reference to FIG. 2, the hose assembly 18 transports material entering the vacuum system to the separator 20. The separator is a collection of parts that receives all the flowing materials and then divides (separates) the flow into essentially two categories of substances: (1) a dry phase material, comprised of gases and aerosols, and (2) a wet phase material, comprised of liquids and solids. Separation is typically accomplished by directing the flowing materials into an internal space, the size and shape of which slows the flow so that relatively heavy materials (the wet phase, which is mostly water) are no longer entrained and drop out of the flow, leaving lighter materials (the dry phase, which is mostly air) to flow separately. Separators that work in this fashion are typically called air-water separators. Some dental vacuum separators are more sophisticated and employ active (motorized) or passive (cyclonic) designs to accomplish separation.

The separator 20 is contained within a housing 36 and includes a wet phase filter assembly 38 and a dry phase filter assembly 40. Each assembly is closed by a removable lid 42 that is sealed via a suitable seal such as an O-ring 44 or the like.

The wet phase filter assembly 38 includes a removable strainer 48 that primarily separates large particles from the material. The size and shape of the inlet 46 serves to slow the flow and drop out the wet phase material by gravity, which then encounters the removable strainer 48. The removable strainer 48 catches "large" (1 millimeter or more) solids and provides a method for retrieving inadvertently aspirated objects, such as crown inlays, orthodontic bands, and the like. The strainer is accessed and removed by first removing the separator housing lid 42. A coarse filter 50 is disposed downstream of the strainer 48, and a fine filter 52 is disposed downstream of the coarse filter 50. The coarse filter 50 and the fine filter 52 are housed together in a removable wet filter cartridge 54.

The wet phase filter assembly 38 includes a first conduit 56 that extends from a liquid buffer space 58 downstream of the strainer 48 to a bottom of the coarse filter 50 as shown in FIG. 2. A second conduit 60 extends from an output space of the coarse filter 50 to a bottom of the fine filter 52. The different pore sizes of the two (or more) filters 50, 52 trap particles of varying size and extend service life. The elements are oriented within the cartridge and housing so that they fill from the bottom up. This arrangement serves to dramatically extend filter service life as compared to filters that fill from the top down or from the sides since filter clogging typically occurs on the filter surface contacted by larger particles. Bottom up filling allows gravity to keep larger particles in the lower portion of the filter leaving the upper surface relatively untouched by larger particles until the filter is full. By comparison, filters that fill from the top or sides allow larger particles to contact and potentially clog the entire filter surface, and thus begin to immediately affect filter flow rates. The wet filter cartridge is serviced by removing the housing lid 42 and strainer 48 and does not require hoses to be detached.

Particulates of varying sizes are trapped in the filter media 50, 52 while wet phase effluent flows into a reservoir or to a drain pump. The wet phase is not only separated from the dry phase, but materials potentially harmful to the environment are separated out so that the wet phase effluent can be safely discharged into a sanitary waste system. Wet phase separation with the separator of the present design successfully traps particles containing mercury (amalgam) to meet established standards for amalgam separator performance. While amalgam separators have been added to prior dental vacuum systems, it is uncommon for a dental vacuum system to include this function as an integral part of its basic design.

The dry phase material flows past the removable strainer 48 and enters the dry phase filter assembly 40. As shown, the dry phase filter assembly includes a plurality of filters arranged in series. In a preferred construction, the dry phase filter assembly 40 is comprised of three filter elements, including a dust filter 62, a HEPA filter 64 and an activated charcoal filter 66. The filters 62, 64, 66 are housed in a dry filter cartridge 68, which is removable from the dry phase filter assembly 40. The dust filter 62 removes gross particulates; the HEPA filter 64 removes smaller particles down to and including most microorganisms; and the charcoal filter 66 removes mercury vapor and other gases that contribute to odors. The dry filter cartridge 68 is serviced by removing the housing lid 42 and does not require hoses to be detached. Materials in the dry phase material potentially harmful to personnel are separated and filtered via the filters 62, 64, 66 so that the dry phase can be safely discharged into an occupied space, such as back into the treatment room. The separator traps mercury vapor, microorganisms, odors and the like to the degree that standards for breathable air are met. As a consequence, power requirements are further reduced since additional piping is not required for exhaust. Additionally, no extra load is placed on the building HVAC system as conditioned air is not exhausted out of the building.

A differential pressure sensor 70 is disposed across an inlet and an exhaust of the dry phase filter assembly 40. The sensor 70 communicates with the controller 21 to provide an indication that the dry filter cartridge 68 requires replacement. The differential pressure sensor 70 responds to changes in pressure (head loss) across the dry phase filter assembly 40. When head loss exceeds a preset value, the detector 70 signals the controller 21 to display a "Dry Cartridge-Change Soon" warning, providing advance notice for the imminent need to replace the cartridge. When the head loss exceeds a preset maximum value, the detector 70 signals the controller 21 to shut off the vacuum producer 12 and display a "Dry Cartridge Full" message.

A similar sensor may be provided for the wet filter cartridge 54. Alternatively, the controller 21 may include a timer or the like that measures a use time and signals that the wet filter cartridge 54 requires replacement after a predetermined use time has elapsed. The filter cartridges 54, 68 can be accessed by removing the housing lids 42. The vertical access to the strainer 48, wet filter cartridge 54 and dry filter cartridge 68 enables the cartridges to be removed upwards (to avoid spillage), which can then be easily replaced.

Since the filter cartridges are easily replaced, customized or specialized filter cartridges with still additional filter components can be designed.

The system of the described embodiments departs from the central dental vacuum system and returns to an in-treatment room system. The fan/motor units address the deficiencies of original treatment room system excess noise and short service life. Flow performance of existing systems is improved by a factor of 2-4, which enables more complete capture of mercury vapor as well as fugitive aerosols and other gases, thereby dramatically improving safety for dental treatment room personnel. Additionally, environmental safety is improved by advanced separation of (1) liquids discharged into a sewer or septic system, and (2) gases discharged back into the treatment room. Liquids discharged meet all ISO standards, while gases discharged meet FDA standards for breathable air. Additional advantages of the system include the evacuator tip engineered to reduce inlet noise, multiple diameter hoses to enable low head loss while maintaining low weight and flexibility, and easily removable and replaceable filter cartridges in the separator.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. An in-treatment room dental vacuum system comprising:
    a vacuum producer comprising a fan/motor unit;
    an operator tool including an evacuator tip;
    a separator coupled with the vacuum producer and disposed upstream of the vacuum producer between the vacuum producer and the operator tool; and
    a hose assembly connecting the operator tool and the separator,
    wherein the separator receives material from the operator tool via the hose assembly, and wherein the separator is configured to separate the material into wet phase material and dry phase material by controlling a flow speed of the material received by the separator and by gravity upstream of any filtering components, and
    wherein the hose assembly comprises multiple diameters including an operator hose having a first diameter coupled with the operator tool and a connection hose having a second diameter larger than the first diameter coupled with the operator hose, the operator hose having a length such that the connection hose is spaced from the operator tool by an amount that renders manipulation of the connection hose during treatment by an operator unnecessary, wherein the fan/motor unit comprises a 0.5 hp or smaller motor, and wherein the operator tool, hose assembly and separator comprise head loss components that effect a target performance value of at least 20 SCFM at the evacuator tip.

2. An in-treatment room dental vacuum system according to claim 1, wherein the separator comprises:
    an inlet receiving a flow of the material from the operator tool via the hose assembly;
    a wet phase filter assembly that receives liquids and heavy solids from the flow, the wet phase filter assembly including a wet filter cartridge; and
    a dry phase filter assembly that receives gases, aerosols and light solids from the flow, the dry phase filter assembly including a dry filter cartridge.

3. An in-treatment room dental vacuum system according to claim 2, wherein the wet phase filter assembly comprises a strainer, a coarse filter disposed downstream of the strainer, and a fine filter disposed downstream of the coarse filter.

4. An in-treatment room dental vacuum system according to claim 3, wherein the coarse filter and the fine filter are housed in the wet filter cartridge.

5. An in-treatment room dental vacuum system according to claim 4, wherein the wet filter cartridge is removable from the wet phase filter assembly.

6. An in-treatment room dental vacuum system according to claim 3, wherein the wet phase filter assembly comprises a first conduit that extends from a liquid buffer space downstream of the strainer to a bottom of the coarse filter.

7. An in-treatment room dental vacuum system according to claim 6, wherein the wet phase filter assembly further comprises a second conduit that extends from a coarse filter output space to a bottom of the fine filter.

8. An in-treatment room dental vacuum system according to claim 2, wherein the dry phase filter assembly comprises a plurality of filters arranged in series.

9. An in-treatment room dental vacuum system according to claim 8, wherein the plurality of filters comprise a dust filter, a HEPA filter, and an activated carbon filter.

10. An in-treatment room dental vacuum system according to claim 8, wherein the plurality of filters are housed in the dry filter cartridge.

11. An in-treatment room dental vacuum system according to claim 10, wherein the dry filter cartridge is removable from the dry phase filter assembly.

12. An in-treatment room dental vacuum system according to claim 2, further comprising:
   a controller cooperable with the vacuum producer and the separator; and
   means for determining that the wet filter cartridge and the dry filter cartridge require replacement, the determining means communicating with the controller.

13. An in-treatment room dental vacuum system according to claim 12, wherein the determining means comprises a timer that measures an operating use time and signals that cartridge replacement is needed after a predetermined use time has elapsed.

14. An in-treatment room dental vacuum system according to claim 12, wherein the determining means comprises a differential pressure sensor disposed across an inlet and an exhaust of the dry phase filter assembly.

15. An in-treatment room dental vacuum system according to claim 1, wherein the first diameter is about 5/8", and wherein the second diameter is about 1".

16. An in-treatment room dental vacuum system comprising:
   a motor having an hp value of 0.5 or less, the motor serving as a vacuum producer;
   a separator coupled with the motor; and
   an operator tool coupled with the separator via a hose assembly, the operator tool including an evacuator tip, and the separator being disposed upstream of the motor and between the motor and the operator tool,
   wherein the operator tool and the hose assembly are constructed to effect a head loss component such that the motor produces a vacuum with a target performance value of at least 20 SCFM at the evacuator tip, and
   wherein the separator receives material from the operator tool via the hose assembly, separates the material into wet phase material and dry phase material by controlling a flow speed of the material received by the separator and by gravity upstream of any filtering components, separately filters the wet phase material and the dry phase material, discharges filtered wet phase material to a drain, and exhausts filtered dry phase material into the treatment room.

17. An in-treatment room dental vacuum system according to claim 16, wherein the hose assembly comprises an operator hose having a first diameter coupled with the operator tool and a connection hose having a second diameter larger than the first diameter coupled with the operator hose, the operator hose having a length such that the connection hose is spaced from the operator tool by an amount that renders manipulation of the connection hose during treatment by an operator unnecessary.

* * * * *